United States Patent
Zlotnik et al.

Patent Number: 5,238,187
Date of Patent: Aug. 24, 1993

[54] LIQUID VAPORIZING, DIFFUSING AND DRIPPING

[75] Inventors: Milton Zlotnik; Arnold Zlotnik, both of West Homestead; John A. Austin, Bakerstown, all of Pa.

[73] Assignee: Surco Products, Inc., Braddock, Pa.

[21] Appl. No.: 772,654

[22] Filed: Oct. 7, 1991

[51] Int. Cl.$^5$ .......................... A61L 9/12; A61L 9/04
[52] U.S. Cl. .......................................... 239/6; 239/39; 239/43; 239/45; 239/50; 239/57; 222/187
[58] Field of Search .................. 239/6, 37, 39, 44, 45, 239/49, 50, 51, 51.5, 57, 43; 222/187

[56] References Cited

U.S. PATENT DOCUMENTS

| | | | |
|---|---|---|---|
| 845,174 | 2/1907 | Hillyard | 239/51 X |
| 917,863 | 4/1909 | Hartwick | 239/50 X |
| 1,063,946 | 6/1913 | Arndt | 239/50 X |
| 1,164,624 | 12/1915 | Appleton | 239/51 X |
| 1,248,859 | 12/1917 | Hitchcock | 239/51 X |
| 2,177,056 | 10/1939 | Crowell | 239/51 X |
| 2,238,935 | 4/1941 | Gumaer | 239/6 |
| 3,633,881 | 1/1972 | Yurdin | 239/44 X |
| 3,746,255 | 7/1973 | Surloff | 239/51 X |

FOREIGN PATENT DOCUMENTS 2052937  2/1981  United Kingdom .................. 239/50

Primary Examiner—Andres Kashnikow
Assistant Examiner—Lesley D. Morris
Attorney, Agent, or Firm—Hymen Diamond

[57] ABSTRACT

Apparatus including a liquid vaporizer having a first wick of linear shape, a bottle for holding the liquid to be vaporized and a gravity-flow metering device having a second wick. The bottle has a closing cap to which two tubes are connected. One tube discharges the liquid from the bottle and the other extends through the cap to the opposite end of the bottle for counteracting the vacuum which is produced when liquid is discharged. The end of the discharging tube extends outwardly of the cap further than the end of the other tube so that a pool is produced in the dispenser. The level of the pool is limited by the position of the end of the tube for counteracting the vacuum. The second wick is of J-shape; one end is immersed in the pool and the other end is suspended over the first wick so that liquid absorbed at the immersed end drips from the second wick on the first wick and is evaporated and diffused from the first wick. There is also disclosed a bottle having a spout with two holes near its end; the lower hole for discharging the liquid and the upper hole for admitting air to counteract the vacuum. There is also disclosed a method of vaporizing and diffusing a liquid whose steps include absorbing a liquid in a first wick and dripping the absorbed liquid on a second wick from which it is vaporized and diffused.

13 Claims, 4 Drawing Sheets

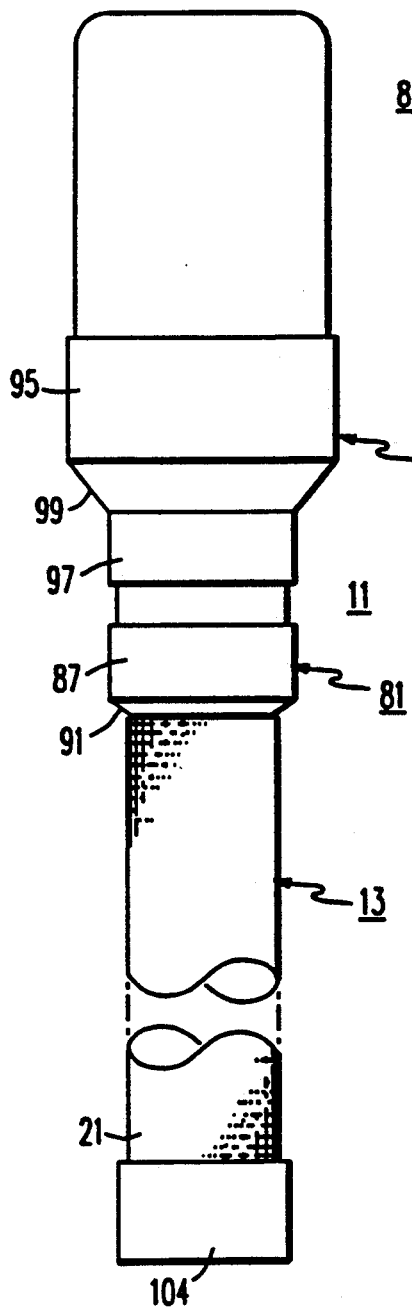
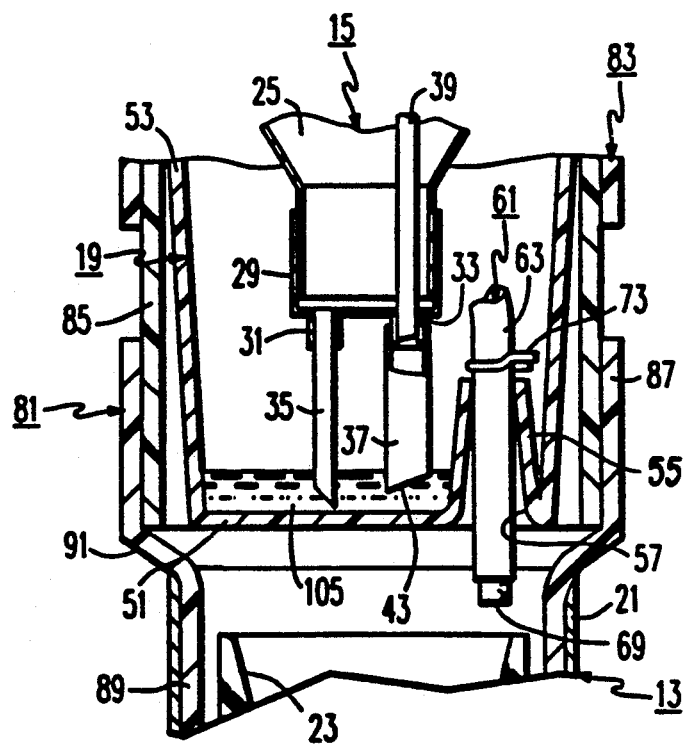
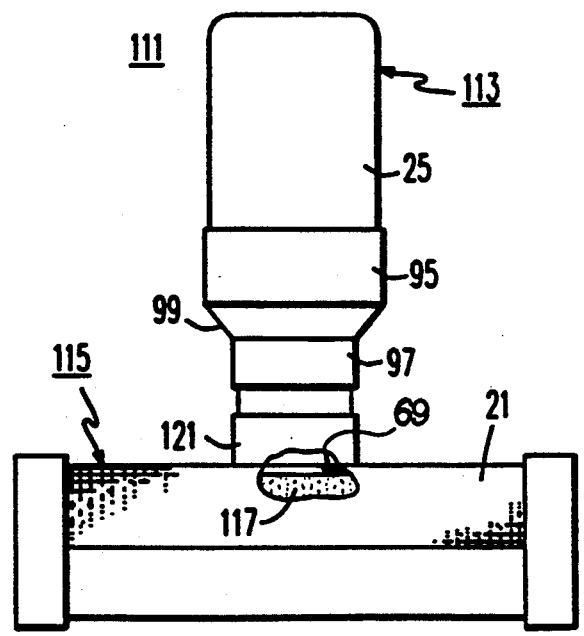

LIQUID VAPORIZING, DIFFUSING AND DRIPPING

BACKGROUND OF THE INVENTION

This invention relates to dispensing of liquids for deodorizing, disinfecting, humidifying or the like. It has particular relationship predominantly to vaporization and diffusing a liquid into a closed region to accomplish these purposes or for dripping a liquid on a predetermined area.

The practice of the prior art relating to this invention is typified by Surloff, U.S. Pat. No. 3,746,255. Surloff discloses apparatus for deodorizing, disinfecting or humidifying a closed region which includes a vaporizer 10 for a liquid. The liquid is fed from a container 15 through a hole 16 on a wick 13 in a perforated body member 11 and is absorbed in the wick and evaporated, the vapor flowing through the member 13 into the closed region where it is diffused. Surloff teaches that the discharge of the liquid is controlled by controlling the replacement air which flows into the container through spout 20 by means of valve 19.

Apparatus of the type disclosed by Surloff has the disadvantage that the liquid in the container which is vaporized must be replaced at frequent intervals of a few days or even a few hours. This deficiency demands frequent attention of service personnel, enhancing the cost of using the apparatus and, in addition, reducing the reliability of the apparatus since it may not serve its purpose when the container is empty and the visit of service personnel is delayed.

It is an object of this invention to overcome the disadvantages of the prior art and to provide apparatus and a method for deodorizing, disinfecting and humidifying a closed region without the demand for frequent replacement of the liquid to be vaporized and the accompanying cost and inconvenience of frequent service. It is also an object of this invention to provide apparatus and a method for dripping a liquid at a predetermined rate from a container without requirement of frequent refilling of the container.

SUMMARY OF THE INVENTION

This invention arises from the discovery that effective control of the discharge of liquid from the prior art container is not feasible. It is prior-art teaching to drip the vaporizable liquid from a hole in the bottom of the container. But, in actual practice, it is not practicable to control the rate at which the liquid flows out of the hole. If the area of the hole is too small, capillary effect inhibits the flow of liquid out of the hole; if the area is larger, the flow out of the container is at an excessive rate so that it is necessary to refill the container frequently, usually at intervals of a few days or a few hours. In addition, where the hole is larger, liquid is deposited on the vaporizing wick at a higher rate than the liquid can be evaporated and the cost of providing the service is enhanced.

In accordance with this invention, the vaporizable liquid is dripped on the wick from which it is vaporized and diffused from a second wick which absorbs the liquid from the container. The apparatus in accordance with this invention, and with which the method of this invention is practiced, includes a container or bottle having a cap through which the liquid flows into a pool whose level is controllably set. An end of a wick of generally J-shape is immersed in the pool and absorbs the liquid. The opposite end of this wick drips the liquid at a controllable rate on the wick from which it is evaporated and diffused.

Specifically, the cap for the bottle supports a first tube through which the liquid discharges into the pool and a second tube which extends through the cap to the opposite end of the bottle and supplies air to counteract the vacuum created as the liquid is discharged through the first tube. The liquid-discharge tube terminates externally to the cap at a greater distance from the cap than the tube which counteracts the vacuum. The liquid discharged from the liquid-discharge tube produces a pool whose level rises until the end of the vacuum-counteracting tube is immersed. At this level of the liquid, the flow of liquid out of the discharge tube is terminated. The level of the pool may be set by adjusting the vacuum-counteracting tube upwardly or downwardly, thus setting the spacing between the ends of the tubes external of the bottle. It is essential that the vacuum-counteracting tube should have an inside diameter (or cross-sectional area) sufficiently large to preclude the blocking of the tube by capillary after the end of this tube is immersed in the liquid. The inside diameter (or cross-sectional area) of the liquid discharge tube should also be of sufficient dimension to preclude the tubes being blocked by capillarity.

The rate at which the wick, which is referred to above as the second wick, drips the liquid on the vaporizing wick is also adjustable. The adjustment is effected by raising or lowering the dripping end of the wick. Raising the dripping end decreases the rate of flow into the vaporizing wick and lowering the end increases the flow into this vaporizing wick.

BRIEF DESCRIPTION OF THE DRAWINGS

For a better understanding of this invention, both as to its organization and as to its method of operation, together with additional objects and advantages thereof, reference is made to the following description taken in connection with the accompanying drawings; in which:

FIG. 2 is a view in side elevation of the apparatus shown in FIG. 1;

FIG. 4 is a fragmental view in longitudinal section showing predominately the structure of the lower part of the bottle and cap by means of which the pool of vaporizable liquid is formed;

FIG. 5 is a view in side elevation showing a modification of this invention.

DETAILED DESCRIPTION OF EMBODIMENTS OF INVENTION

Figure 1:
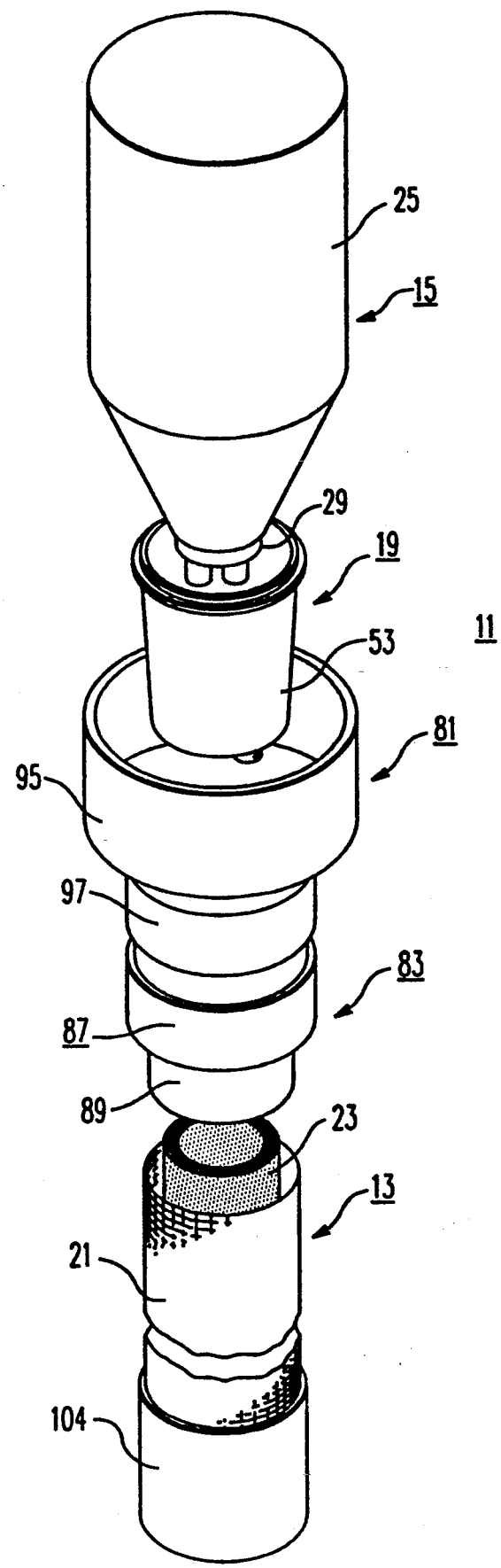
FIG. 1 is an exploded view in isometric of apparatus in accordance with this invention and for practicing the method of this invention.

FIGS. 1 through 4 show vaporizing and diffusing apparatus 11 for deodorizing, disinfecting or humidifying, or for otherwise treating the atmosphere in, a closed region. The apparatus 11 includes a vaporizer 13, a container or bottle 15 for supplying a liquid 17 (FIG. 3) to be vaporized and diffused, and a gravity-flow metering device 19, which is sometimes referred to as a gravity-drip dispenser.

The vaporizer 13 includes an elongated foraminous tube 21 of generally circular transverse cross-section. This tube is composed typically or perforate sheet metal or wire mesh. Within the tube 21 an elongated generally circularly-cylindrical wick 23 is supported. The wick 23 is composed of a highly porous and absorbent material. It is typically composed of porous or fibrous styrofoam, cellulose or plastic, or the like compounded, e.g., natural or synthetic textile material. The wick 23 is supported by the wall of the tube 21 and in the case of a vertical structure, by a container 104 for collecting surplus liquid. Typically, the wick may be procured from Smithers Oasis of Kent, Ohio as absorbent foam.

Figure 3:
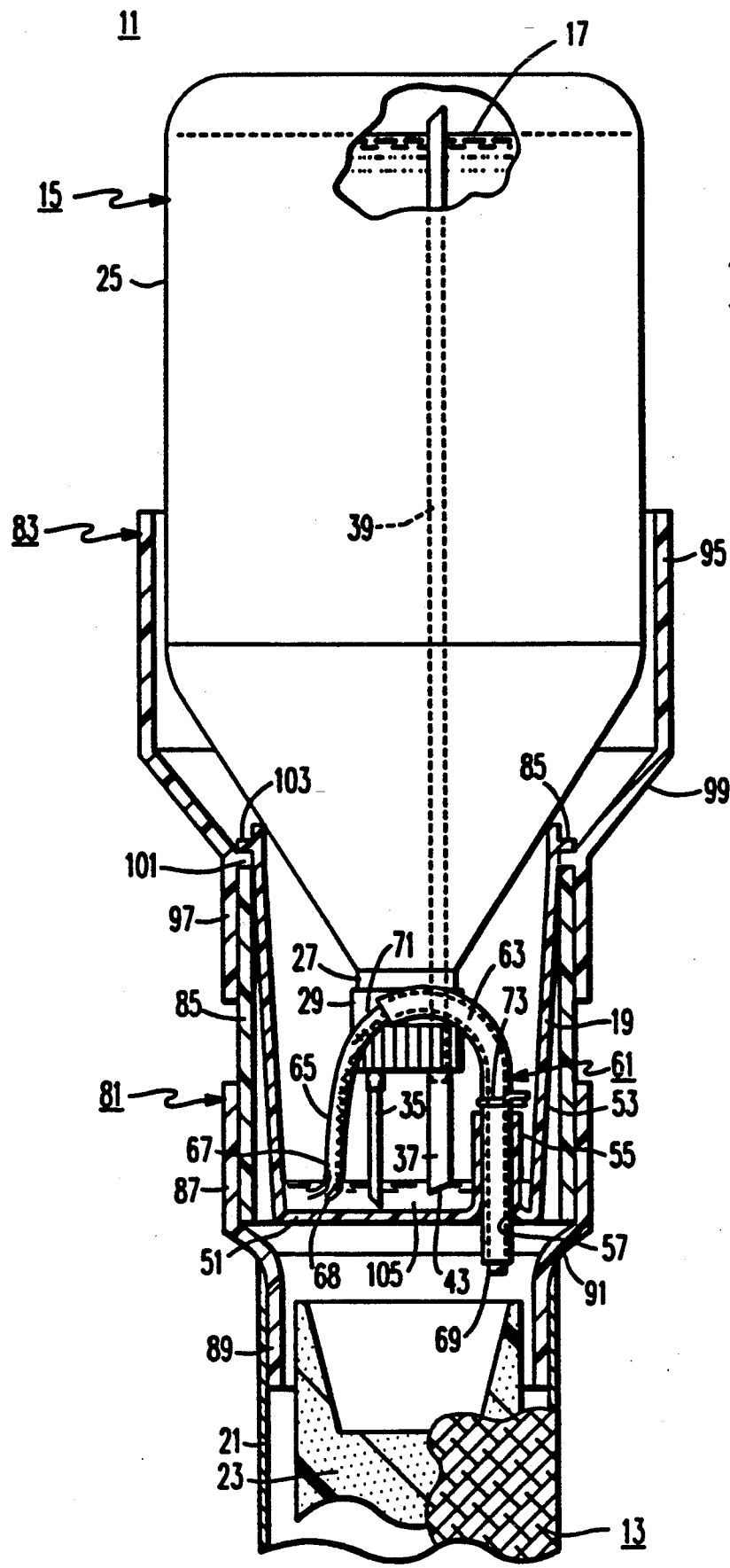
FIG. 3 is a view in longitudinal section, broken off at the bottom of the apparatus shown in FIG. 1 with some of the parts shown not sectioned in the interest of clarity and with a part broken away to show internal structure.

The bottle 15 has a generally circularly-cylindrical body 25, terminating in a section having the shape of a frustrum of a cone, which section in turn merges into a generally circularly-cylindrical tip 27 (FIG. 3) to which a cap 29 is secured liquid-tight. The tip 27 may be threaded externally and the cap 29 internally and the cap may be screwed onto the tip or the cap may be a tight removable fit on the tip as shown in FIGS. 3 and 4. The body 25 of the bottle 15 is composed of a strong plastic material; typically heavy duty polypropylene or polyethylene.

Hollow projections 31 and 33 (FIG. 4) of generally circular transverse cross-section extend integrally rom the base of the cap 29. Projection 31 carries a tube 35 which is typically a press-fit in the projection and thus is secured in the projection. Projection 33 carries a sleeve 37 which is secured externally to this projection, typically by a press-fit. The tube 35 terminates flush with the internal surface of the base of cap 29 and discharges the liquid in the bottle 15. Sleeve 37 is coaxial or coextensive with a tube 39 which is a press-fit in the projection 33 (FIG. 4). Tube 39 extends substantially to the internal end of body 25 opposite the cap 29. The tube 35 extends externally of the bottle 15 from the cap 29 a greater distance than the end 43 of sleeve 27 which is in communication with tube 39. Sleeve 37 and tube 39 conduct air into the bottle to counteract the vacuum created as the level of the liquid in the bottle falls. The tube 35 and the sleeve 37 are bevelled at the bottom to reduce the capillary effect.

The gravity-flow metering unit 19 or gravity-drip dispenser is essentially a cup having a circular base 51 from which the side 53 of generally circular, transverse cross-section tapers upwardly. A tube-like projection 55 of generally circular, transverse cross-section, molded integrally with the base, extends from the base 51 near its periphery. The projection merges with the base communicating with an opening 57 in the base. The base 51 and side 53 of the gravity-drip dispenser are composed typically of a strong plastic; typically heavy-duty polypropylene or polethylene. The gravity-drip dispenser also includes a wick assembly 61 which is supported in the projection 55. The wick assembly includes a sleeve 63 through which a wick 65 of generally J-shape extends. The sleeve 63 is composed of plastic and typically has a configuration of an arc of a helix formed by winding a plastic tube on a mandrel. The wick 65 extends through the projection 55, with one end 67 (FIG. 3) near the base 51 below liquid level and the opposite end 69 also below liquid level, typically below the base 51. The end 67 terminates in a generally horizontal tip 68 of strands of the fabric of the wick. The sleeve 63 is a loose fit in the projection 55 and is slideable together with the part of the wick within it, upwardly or downwardly in the projection, thus raising or lowering predominantly the cross-member 71 of the J. The sleeve 63 and the wick 65 within it are held in any selected position by a clamp 73 which engages the sleeve near the top of projection 55. The wick 65 is composed of liquid-absorbing material which absorbs the liquid and passes it by capillarity to the end 69 whence the liquid is passed to the wick 23. Essentially the wick 65 operates like a syphon in passing the liquid. The liquid may drip or flow slowly. The wick 65 is composed typically of a natural or synthetic fibrous felt. Typically a fiberglass-coated cotton fiber wick, which may be procured from EZ-Fit Corporation of 613 Washington Street, Morris, Ill. 60450, is used.

The vaporizer 13, the gravity-drip dispenser 19 and the bottle 15 are mounted together as a unit by a lower bracket 81 and upper bracket 83, each in the general shape of a cup open at both ends, and by a cylindrical member 85. The brackets 81 and 83 and the member 85 are composed of a strong plastic; typically polyvinyl chloride. The brackets 81 and 83, as well as the vaporizer 13, may be provided with facilities (not shown) for mounting on the wall or suspending from the ceiling of the closed region to be deodorized, disinfected or humidified.

The bracket 81 includes cylindrical sections 87 and 89 of generally circular, transverse cross-section and of larger and smaller diameters, respectively, joined by a section 91 generally in the shape of a frustrum of a cone; the joints between sections 89 and 91 are rounded. The bracket 81 is seated on the upper edge of the perforated tube 21 of the evaporator 13, with the edge engaging the conical section 91 at the joint between the conical section 91 and the lower section 89 and the lower section in engagement with the inner wall of tube 21. The top edge of tube 21 is tapered to match the slope of the section 91. The cylinder 85 is seated on the inner surface of the tapered section 91 at the joint between this section and the upper section 81.

The bracket 83 has an upper section 95 of larger diameter and a lower section 97 of smaller diameter, joined by a section 99 having the shape generally of the frustrum of a cone. An annular projection 101 extends inwardly from the lower section 97 at its joint with the conical section 99. The bracket 83 is supported on the upper edge of the cylinder 85 with the annular projection 101, engaging the upper edge of the cylinder and the inner wall of the lower section 97, engaging the outer wall of the cylinder 85 in a sliding fit. Near the top, the side 53 of the gravity-drip dispenser 19 is seated on the inward annular projection 101 with projection 103 engaging the upper surface of the projection 101. The bracket 83, the cylinder 85 and the gravity-drip dispenser are thus locked together with the projection 101 engaged between the projection 103 and the upper edge of cylinder 85. As shown in FIGS. 1 and 2, the apparatus 11 includes a container 104 which is mounted on the lower end of the vaporizer 13 to receive any liquid which is dripped on wick 23 but not vaporized. Where the apparatus is mounted vertically, the container 103 serves to support the wick 23.

In the use of the apparatus shown in FIGS. 1 through 4, in the practice of this invention, the liquid to be vaporized is discharged from bottle 15 through tube 35 (FIG. 4) into gravity-drip dispenser 19, forming a pool 105 in the dispenser. So long as the opening in the end 43 of sleeve 37 is above the upper level of the pool, air is drawn into the bottle 25 above the level of the liquid at the top as this level drops. The air counteracts the vacuum created by the drop in this level and the liquid continues to flow out of tub 35. Once the level of the pool 105 rises above the opening in the end of sleeve 43, the flow of air into the bottle 35 is blocked and the flow of liquid through tube 35 is blocked. The pool 105 has reached its highest level.

The wick assembly 61 is so positioned in the gravity-drip dispenser 19 that the end 67 of the wick 65 and the horizontal tip 68 (FIG. 3) are immersed in the pool 105. The wick absorbs the liquid from the pool and the liquid drips or flows slowly through end 69 onto wick 23 whence it is evaporated and diffused in the closed region. The rate at which liquid is dripped or flows onto wick 23 is effectively controlled by releasing clamp 73 and raising or lowering the end of the wick assembly 61 and the cross member 71 of the J attached to it. Raising the end of the wick assembly and the cross-member reduces the rate at which liquid is deposited on wick 23; lowering these portions increases the rate. The rate of evaporation and diffusion of the liquid may thus be set or metered and once set, the operation continues automatically without the intervention of service personnel. Frequent replacement or filling of the bottle 15 is not required. A bottle holding a gallon of the liquid will continue to operate automatically for about one month without the intervention of service personnel.

For proper practice of this invention, it is essential that the inside diameter of the tubes 35 and 37 be of sufficient magnitude to preclude blocking of flow by reason of capillarity. Typically, tube 39 has an inside diameter of ¼-inch and an outside diameter of ⅜-inch and tube 35 has an inside diameter of 3/16-inch and an outside diameter of ¼-inch. The bevelled ends reduce the capillary effect.

The modification of this invention shown in FIG. 5 is apparatus 111 which is similar to the apparatus shown in FIGS 1 through 4, except that a bottle 113 similar to the bottle 15 is mounted transversely to a vaporizer 115 and discharges liquid by dripping from a wick 65 (not shown in FIG. 5) 63 on a wick 117 intermediate the ends of wick 117. The apparatus 111 includes, in addition to the vaporizer 115, the bottle 113 and the gravity-drip dispenser 19 (not shown in FIG. 5), the latter mounted together similarly to the same components of the FIG. 1 apparatus. But the assembly of the bottle 113 and the gravity-drip dispenser is mounted or seated on a cylinder 121, projecting upwardly from the vaporizer 115 intermediate its ends. The gravity-drip dispenser 19 is the same as the dispenser of FIGS. 1 through 4.

Figure 6:
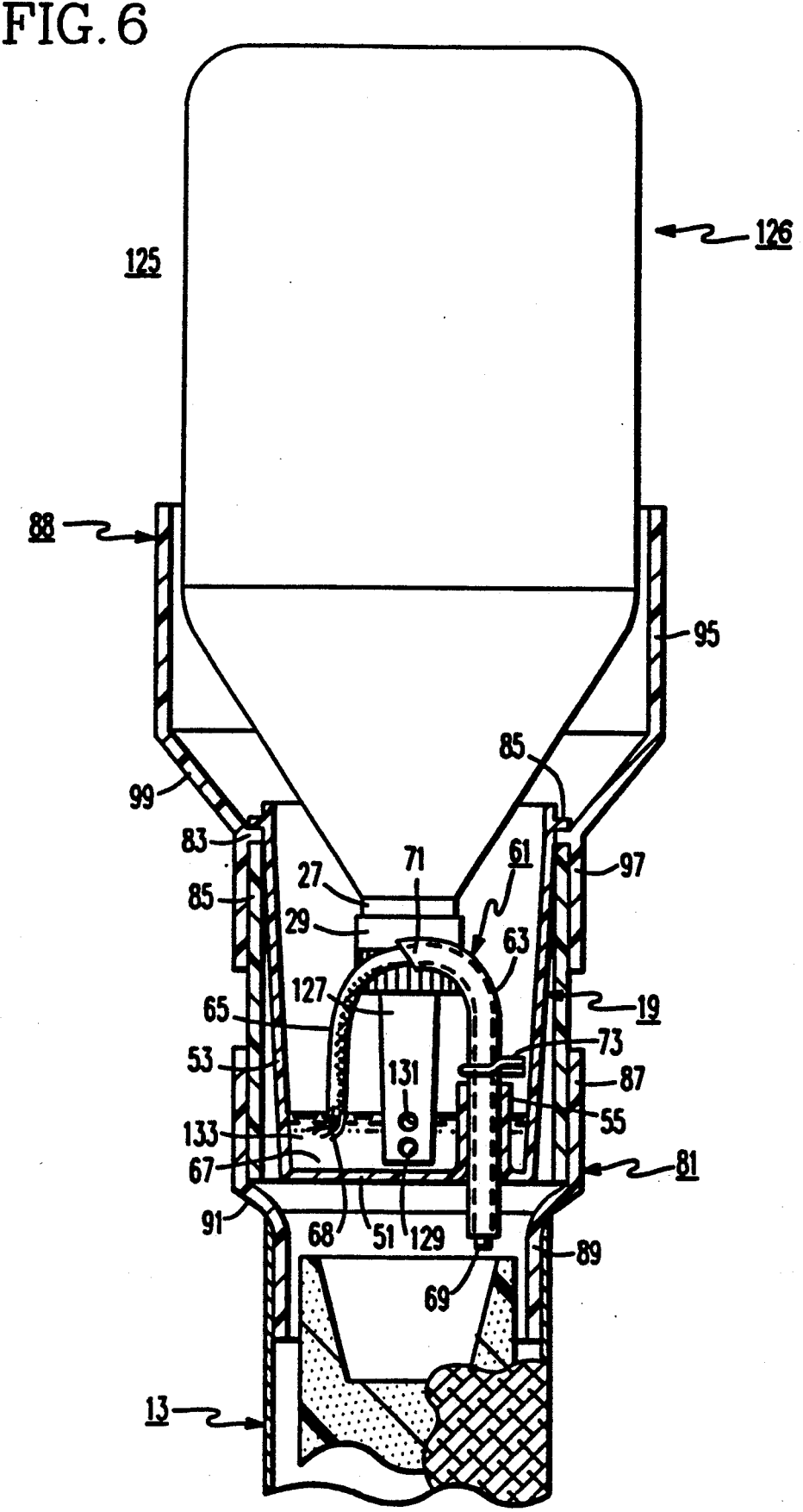
FIG. 6 is a view in longitudinal section, similar to FIG. 3, showing another modification of this invention.

The modification shown in FIG. 6 is apparatus 125, similar to the apparatus 11 of FIG. 1 through 4 except that its bottle 126 has a spout 127 instead of the tubes 35 and 39. The spout 127 is closed at the bottom. It has holes 129 and 131 near the bottom. The holes 129 and 131 open into the spout 127; they are not through holes. Liquid flows t form pool 133, predominately through the lower hole 129. As the level of the liquid in bottle 127 falls, a vacuum is produced which sucks air in through hole 131 until the level of pool 133 rises above the hole 131.

The assembly consisting of the bottle 15 and gravity-drip dispenser 19 or the bottle 126 and the gravity-drip dispenser 19 constitute a unit which may be used separately from the apparatus 11 or 125 to drip liquid in measured quantities where necessary.

While preferred embodiments and preferred practice of this invention have been disclosed herein, many modifications thereof are feasible. This invention is not to be restricted except insofar as is necessitated by the spirit of the prior art. It is to be understood that any practice of this invention or adaptation of its principle which escapes the precise wording of the claims is regarded as within the scope of equivalents of this invention.

We claim:

1. The method of deodorizing, disinfecting or humidifying an enclosed region; including: absorbing in a first wick a liquid to be vaporized for deodorizing, disinfecting or humidifying the region, by discharging the liquid from said first wick on a second wick, absorbing the liquid in said second wick, and vaporizing, and diffusing the vapor from, said liquid from said second wick in said region; said method being characterized by the steps of producing a pool of the liquid, maintaining the pool below a predetermined level, positioning said first wick in said pool to absorb the liquid from said pool, said metering the rate at which said liquid vaporized by adjusting the position of said first wick in said pool.

2. Liquid vaporizing and diffusing apparatus including a vaporizer having a first wick for absorbing liquid to be vaporized and diffused by said vaporizer a liquid-holding container, a gravity-drip dispenser interposed between said vaporizer and said container, means, connected to said container, for discharging the liquid therein in a pool in said gravity-drip dispenser, a second wick, means, connected to said gravity-drip dispenser, for positioning said second wick in liquid-absorbing relationship in said pool and in interconnecting relationship between said container and said first wick for absorbing liquid in said second wick from said pool and discharging said liquid gradually on said first wick for vaporization and diffusion by said vaporizer, said positioning means including means adapted to permit the adjusting of the position of said second wick in said pool to meter the rate at which said liquid is discharged from said second wick on said first wick whereby the second wick may be adjusted to produce a rate of vaporization and diffusion such that once adjusted, the vaporization and diffusion in said region continues automatically for a long interval of time, such as one month, without servicing.

3. The liquid vaporizing and diffusing apparatus of claim 1 wherein the liquid-holding container is a bottle having a cap at one end and having a first tube connected to said cap for discharging liquid from said bottle into said gravity-drip dispenser and also having a second tube extending through said cap to the other end of said bottle for counteracting the vacuum produced when liquid is discharged from said bottle, said second tube terminating externally to said cap at a smaller distance from said cap than said first tube, thereby to set the maximum level of the pool.

4. The liquid vaporizing and diffusing apparatus of claim 2 wherein the liquid-holding container includes means, connected to said container, for maintaining the level of the pool at or below a predetermined height.

5. The liquid vaporizing and diffusing apparatus of claim 2 wherein the liquid-holding container is a bottle having a spout for discharging the liquid from the bottle into the gravity-drip dispenser, said spout having a first transverse opening at a predetermined distance from the end of said spout for discharging said liquid into said pool and also having a second transverse opening at a greater distance than said predetermined distance from the end of said spout for admitting air into said bottle to counteract the vacuum produced as liquid is discharged from said bottle.

6. Liquid vaporizing and diffusing apparatus including a vaporizer having a first wick for absorbing liquid to be vaporized and diffused by said vaporizer, a liquid-holding container and a gravity-drip dispenser, said dispenser having a second wick therein, and means mounting said gravity-drip dispenser interposed between said liquid-holding container and said vaporizer to receive liquid discharged from said liquid-holding container for absorbing the liquid in said second wick, said second wick being so positioned with respect to said first wick as to discharge the absorbed liquid at a first predetermined rate to said first wick for vaporization and diffusion by said vaporizer whereby the liquid in said liquid-holding container is automatically, without the intervention of service personnel, vaporized and diffused over an extended time interval at a predetermined rate which is dependent on said first predetermined rate; said liquid-holding container including means, connected to said container, for discharging said liquid in a pool in the gravity-drip dispenser, and said gravity-drip dispenser including means, connected to said dispenser, for positioning said second wick in liquid-absorbing relationship with said pool, and said positioning means including means for setting the position of said second wick in said pool to set the rate of vaporization of diffusion of said liquid, said liquid-holding container being a bottle having a cap at one end and having a first tube connected to said cap for discharging liquid from said bottle into said gravity-drip dispenser and also having a second tube extending through said cap to the other end of said bottle for counteracting the vacuum produced when liquid is discharged from said bottle, said second tube terminating externally to said cap at a smaller distance from said cap than said first tube thereby to set the maximum level of said pool, said first tube having an inside diameter of sufficient magnitude to preclude blocking of the discharge of said liquid by reason of capillarity and said second tube having an inside diameter of sufficient magnitude to preclude by reason of capillarity the blocking of the flow of air to counteract the vacuum.

7. The article for use in supplying liquid in apparatus for deodorizing, disinfecting or humidifying a closed region; said article including: a bottle having a closing cap at one end, a first tube for admitting air in said bottle counteract the vacuum produced when liquid is discharged from said bottle, said tube extending through said cap and terminating near the opposite end of said bottle, and a second tube for discharging the liquid from said bottle extending from said cap in transmitting relationship with the liquid, said first and second tubes each having an inside diameter of sufficient magnitude to preclude the blocking of said tubes by capillarity.

8. For use in discharging a liquid at a predetermined rate, the combination including:
(a) a bottle for holding said liquid having a closing cap at one end thereof, a first tube, connected to said cap, for discharging liquid from said bottle, a second tube, connected to said cap, extending into said bottle from said one end substantially to the opposite end for counteracting the vacuum produced in said bottle as liquid is discharged therefrom;
(b) a gravity-drip dispenser;
(c) means mounting said bottle in liquid-discharge communication with said dispenser through said first tube to form a pool of said discharged liquid in said dispenser; and
(d) a wick, connected to said dispenser positioned with one end extending into said pool and the other end disposed to discharge the liquid from said pool from said other end; said first and second tubes being connected to said cap, with said one end of said first tube extending outwardly of said cap a greater distance from said cap than the end of said second tube extends outeardly of said cap, thereby to set the maximum height of said pool; said first and second tubes each having an inside diameter of sufficient magnitude to preclude the blocking of said tubes by capillarity.

9. An article for use in supplying liquid in apparatus for deodorizing, disinfecting or humidifying a closed region; said article including: a bottle having a closing cap at one end, a first tube for admitting air in said bottle to counteract the vacuum produced when liquid is discharged from said bottle, said tube extending through said cap and terminating near the opposite end of said bottle, and a second tube for discharging the liquid from said bottle extending from said cap in transmitting relationship with the liquid, said first and second tubes each being beveled at their discharging ends to suppress blocking of said tubes by capillarity.

10. For use in discharging a liquid at predetermined rate, the combination including:
(a) a bottle for holding said liquid having a closing cap at one end thereof, a first tube, connected to said cap, for discharging liquid from said bottle, a second tube, connected to said cap, extending into said bottle from said one end substantially to the opposite end for counteracting the vacuum produced in said bottle as liquid is discharged therefrom;
(b) a gravity-drip dispenser;
(c) means mounting said bottle in liquid-discharge communication with said dispenser through said first tube to form a pool of said discharged liquid in said dispenser; and
(d) a wick, connected to said dispenser positioned with one end extending into said pool and the other end disposed to discharge the liquid from said pool from said other end of said wick;
said first and second tubes being connected to said cap with said one end of said first tube extending outwardly of said cap a greater distance from said cap than the end of said second tube extends outwardly of said cap, thereby to set the maximum height of said pool; said first and second tubes each being beveled at their discharging ends to suppress blocking of said tubes by capillarity.

11. For use in discharging a liquid at a predetermine rate; the combination including:
(a) a bottle for holding said liquid having closing means at one end thereof, a first tube, connected to said closing means, for discharging liquid from said bottle, a second tube, connected to said closing means, extending into said bottle from said one end substantially to the opposite end for counteracting the vacuum produced in said bottle as liquid is discharged therefrom;
(b) a gravity-drip dispenser, said gravity-drip dispenser including a tube-like projection which extends from, and is in communication with, an opening in the base of the gravity-drip dispenser;

(c) means mounting said bottle in liquid-discharge communication with said dispenser through said first tube to form a pool of said discharged liquid in said dispenser; and (d) a wick and means, connected to said dispenser, for positioning said wick with one end extending into said pool and the other end extending into said tube-like projection to discharge the liquid from said pool from said other end; said tube-like projection having a length such that its end inwardly of said base is above said one end of said wick; said positioning means being adapted to vary the position of said wick with respect to said pool thereby to vary the rate of discharge of said liquid from said pool through said other end, said first and second tubes being connected to said closing means with the end of said first tube extending outwardly of said closing means a greater distance from said closing means than the end of the second tube extends outwardly of said closing means, thereby to set the maximum height of said pool.

12. Liquid vaporizing and diffusing apparatus including a vaporizer having a first wick for absorbing liquid to be vaporized and diffused by said vaporizer, a liquid-holding container, and means, including a second wick, interconnecting said liquid-holding container and said vaporizer with said second wick for absorbing liquid in said second wick from said liquid-holding container and discharging said liquid absorbed gradually in said first wick for vaporization and diffusion by said vaporizer; said interconnecting means between said liquid-holding container and said vaporizer including a gravity-drip dispenser and said liquid-holding container including means for discharging liquid from said liquid-holding container into said dispenser for forming a pool in said dispenser, said liquid-holding container also including means for maintaining the surface of said pool below a predetermined level, said gravity-drip dispenser also having a base having an opening therein communication with which a tube-like projection extends inwardly of said gravity-drip dispenser, the end of said projection inwardly of said base extending above said level, said second wick being disposed in liquid-absorbing relationship with said pool with is one end in said pool and its opposite end in said tube-like projection in liquid-discharging relationship with said first wick through said opening in said base; said interconnecting means also including, means, connected to said second wick, for metering the rate at which said liquid is discharged in said first wick, whereby the liquid in said liquid-holding container is automatically, without the intervention of service personnel, vaporized and diffused over an extended time interval at a predetermined rate determined by the rate at which said liquid is discharged on said first wick as metered by said metering means.

13. Liquid vaporizing and diffusing apparatus including a vaporizer having a first wick for absorbing liquid to be vaporized and diffused by said vaporizer, a liquid-holding container, a gravity-drip dispenser interposed between said vaporizer and said container, means, connected to said container, for discharging the liquid therein in a pool in said gravity-drip dispenser, means, connected to said container, for maintaining the surface of said pool below a predetermined level, said gravity-drip dispenser having a base having an opening therein in communication with which a tube like projection extends inwardly of said dispenser, the inner end of said projection being above said level of said pool, a second wick, means, connected to said gravity-drip dispenser, for positioning said second wick in liquid-absorbing relationship in said pool and in interconnecting relationship between said container and said first wick, for absorbing liquid in said second wick from said pool and discharging said liquid gradually on said first wick for vaporization and diffusion by said vaporizer, said positioning means positioning said second wick with one end in said pool and the other end in said projection in discharge relationship with said first wick, said positioning means including means adapted to permit the adjusting of the position of said second wick in said pool to meter the rate at which said liquid is discharged from said second wick on said first wick thereby said second wick may be adjusted to produce a rate of vaporization and diffusion such that once adjusted, the vaporization and diffusion in said region continues automatically for a long interval of time, such as one month, without servicing.

* * * * *